United States Patent [19]
Turcott

[11] Patent Number: 5,941,831
[45] Date of Patent: Aug. 24, 1999

[54] METHOD FOR DIAGNOSING CARDIAC ARRHYTHMIAS USING INTERVAL IRREGULARITY

[75] Inventor: Robert Turcott, Menlo Park, Calif.

[73] Assignee: Pacesetter, Inc., Sunnyvale, Calif.

[21] Appl. No.: 09/054,929

[22] Filed: Apr. 3, 1998

[51] Int. Cl.$^6$ .................................................. A61B 5/0468
[52] U.S. Cl. ......................................................... 600/515
[58] Field of Search ..................................... 600/515, 519

[56] References Cited

U.S. PATENT DOCUMENTS

| | | | |
|---|---|---|---|
| 3,618,593 | 11/1971 | Nachev et al. ........................... | 600/515 |
| 4,202,340 | 5/1980 | Langer et al. ........................... | 128/419 |
| 4,880,005 | 11/1989 | Pless et al. ............................... | 128/419 |
| 4,971,058 | 11/1990 | Pless et al. ............................... | 128/419 |
| 5,086,772 | 2/1992 | Larnard et al. .......................... | 128/419 |
| 5,107,850 | 4/1992 | Olive ......................................... | 128/705 |
| 5,191,524 | 3/1993 | Pincus et al. ............................ | 600/519 |
| 5,350,406 | 9/1994 | Nitzsche ................................... | 607/14 |
| 5,411,031 | 5/1995 | Yamtov ..................................... | 600/519 |
| 5,462,060 | 10/1995 | Nitzsche et al. ......................... | 128/702 |
| 5,628,326 | 5/1997 | Arand et al. .............................. | 600/519 |

OTHER PUBLICATIONS

Physician's Manual for VENTAK PRx II 1715/1710; 1994; pp. 23–26.

*Primary Examiner*—William E. Kamm
*Attorney, Agent, or Firm*—Steven M. Mitchell

[57] ABSTRACT

A method for detecting or classifying cardiac arrhythmias using interval irregularity. The method includes the steps of detecting a patient's cardiac activity and looking at a first selected criterion such as the patient's heart rate exceeding a preset rate threshold to determine if a tachycardia is present. When the first criterion is met, a window of N successive cardiac intervals is selected for analysis. A selected number of the shortest and longest intervals are ignored and the difference between the remaining longest and shortest intervals is calculated to provide a measure of interval irregularity indicative of the origin of the cardiac rhythm. In one embodiment, a parameter n is set such that $0 \leq n < N/2$, and the intervals in the window are ordered from shortest to longest with the shortest being interval 1 and the longest being interval N. The difference between interval N−n and interval n+1 is then computed to provide a measure of interval irregularity which is indicative of the origin of a cardiac rhythm. For example, if n=1, the longest and shortest of the intervals in a window of intervals are discarded, and the difference between the duration of the second longest and second shortest is calculated and this difference is a measure of interval irregularity. The difference is compared to a selected irregularity threshold and if the difference is greater than the threshold, the rhythm is considered irregular. If the difference is less than or equal to the irregularity threshold, the rhythm is considered regular.

6 Claims, 1 Drawing Sheet

METHOD FOR DIAGNOSING CARDIAC ARRHYTHMIAS USING INTERVAL IRREGULARITY

BACKGROUND OF THE INVENTION

The present invention relates generally to the field of cardiac therapy devices, and particularly to a tachyarrhythmia detection (diagnostic) algorithm.

Implantable cardioverter defibrillators (ICDs) are highly sophisticated medical devices which are surgically implanted (abdominally or pectorally) in a patient to monitor the cardiac activity of the patient's heart, and to deliver electrical stimulation as required to correct cardiac arrhythmias which occur due to disturbances in the normal pattern of electrical conduction within the heart muscle.

Cardiac arrhythmias can generally be thought of as disturbances of the normal rhythm of the heart beat. Cardiac arrhythmias are broadly divided into two major categories, namely, bradyarrhythmia and tachyarrhythmia. Tachyarrhythmia can be broadly defined as an abnormally rapid heart rate (e.g., over 100 beats/minute, at rest), and bradyarrhythmia can be broadly defined as an abnormally slow heart rate (e.g., less than 50 beats/minute). A normal cardiac rhythm (e.g., between 50–100 beats/minute) is referred to as a "sinus rhythm".

Tachyarrhythmias are further subdivided into two major sub-categories, namely, tachycardia and fibrillation. Tachycardia is a condition in which the electrical activity and rhythms of the heart are rapid, but organized. Fibrillation is a condition in which the electrical activity and rhythm of the heart are rapid, chaotic, and disorganized.

Tachycardia and fibrillation are further classified according to their location within the heart, namely, either atrial or ventricular. In general, atrial arrhythmias are not life-threatening, because the atria (upper chambers of the heart) are only responsible for aiding the movement of blood into the ventricles (lower chambers of the heart), whereas ventricular arrhythmias are life-threatening, because if the ventricles become arrhythmic, the heart's ability to pump blood to the rest of the body is impaired. The most serious and immediately life-threatening type of cardiac arrhythmia is ventricular fibrillation, in which the electrical activity of the ventricles becomes so random and chaotic that the heart rapidly becomes unable to pump sufficient blood to sustain life.

In general, an ICD continuously monitors the heart activity of the patient in whom the device is implanted by analyzing electrical signals, known as electrograms (EGMs), generated by sensing electrodes positioned proximate to the sino-atrial and/or atrio-ventricular node of the patient's heart, and, most advantageously, in the right ventricular apex of the patient's heart. More particularly, contemporary ICDs include waveform digitization circuitry which digitizes the analog EGM produced by the sensing electrodes, and a microprocessor and associated peripheral ICs which analyze the thusly digitized EGM in accordance with a diagnostic or detection algorithm implemented by software stored in the microprocessor. Contemporary ICDs are generally capable of diagnosing (detecting) the various types of cardiac arrhythmias discussed above, and then delivering the appropriate electrical energy/therapy to the patient's heart, in accordance with a therapy delivery algorithm also implemented in software stored in the microprocessor, to thereby convert or terminate the diagnosed arrhythmia.

In such ICDs, it is imperative that the detection or diagnostic algorithm employed be reliably accurate, so that the patient's heart condition can be accurately monitored at all times and any arrhythmias promptly and properly diagnosed and treated (by delivery of the appropriate therapy to terminate or convert the detected arrhythmia). In this regard, there are a number of presently available or known detection algorithms which, for the most part, are quite reliable and accurate.

For example, U.S. Pat. No. 4,971,058, issued to Pless et al. and assigned to the assignee of the present invention, the disclosure of which is incorporated herein by reference, discloses a detection algorithm (hereinafter referred to as "the '058 detection algorithm") which determines the duration of the intervals between successive heartbeats (i.e., cycle lengths between consecutive QRS complexes), and computes a running average of the duration of a prescribed number (e.g., 4) of preceding intervals, referred to as the "average interval", which is re-computed (updated) every interval (i.e., on an interval-by-interval basis). These computed average intervals are used in providing a rhythm diagnosis.

Obviously, a misdiagnosis of sinus tachycardia such as results from exercise as ventricular tachycardia would result in a subsequent delivery of therapy (treatment) which is inappropriate. If therapy is delivered that is not required it may actually induce an arrhythmia that really does require treatment, and, at a minimum, will result in a waste of the finite amount of energy that the device is capable of delivering over its lifetime, thereby shortening its useful lifetime.

One algorithm which is know for diagnosing cardiac rhythms and particularly ventricular tachycardia is called rate stability or interval irregularity. The basic idea is that the interbeat intervals in a normal cardiac rhythm are not regular, i.e., they typically vary from one to the next. However, the interbeat intervals for certain arrhythmias and in particular intervals for successive ventricular tachycardia rhythms tend to be quite regular or stable. It is thus known to look at the variation from one interval to the next to diagnose ventricular tachycardia. Such a diagnostic algorithm is disclosed in U.S. Pat. No. 4,830,006 to Haluska et al, which patent is incorporated herein by reference. An interval irregularity measure may also be used to distinguish atrial fibrillation, which may produce greater interval irregularity, from monomorphic VT which is typically regular.

One problem with prior rate stability algorithms is that they are more computationally demanding than is desirable in an implanted device having a finite energy supply from its battery. Further, some prior art algorithms may be sensitive to cardiac sensing errors.

It is therefore an object of the invention to provide an improved interval irregularity diagnostic algorithm.

It is another object of the invention to provide an interval irregularity algorithm which is less sensitive to cardiac sensing errors.

It is still another object of the invention to provide an interval irregularity algorithm which is not computationally demanding.

SUMMARY OF THE INVENTION

The present invention encompasses a method for detecting the origin of cardiac rhythms which includes the steps of detecting a patient's cardiac activity, determining from the detected cardiac activity if measured heartbeat intervals satisfy a selected criterion such as the patient's heart rate exceeding a preselected tachycardia rate threshold, selecting a window of successive cardiac intervals, ignoring a selected number of the shortest and longest ones of the intervals, and taking the difference between the remaining longest and shortest intervals to provide a measure of interval irregularity indicative of the origin of a cardiac rhythm.

In a first embodiment of the invention, a window of N successive cardiac intervals is selected, a preset parameter n is used such that $0 \leq n < N/2$, and the step of ignoring a selected number of the shortest and longest intervals includes sorting or ordering the intervals in the window from shortest to longest with the shortest being interval 1 and the longest being interval N, and taking the difference between interval N−n and interval n+1. The first selected criterion can be the heart rate exceeding a preset tachycardia rate threshold. For example, if n=1, the longest and shortest of the intervals in a window of intervals are discarded, and the difference between the duration of the second longest and second shortest is calculated and this difference is a measure of interval irregularity. The difference may then be compared to a selected irregularity threshold and if the difference is greater than or equal to the threshold, the rhythm is considered irregular and thus not of ventricular origin. If the difference is shorter than the irregularity threshold, the rhythm is considered regular and thus of ventricular origin. Other algorithms for analyzing the intervals which ignore the selected number of the shortest and longest intervals may also be used.

BRIEF DESCRIPTION OF THE DRAWINGS

These and various other features and advantages of the present invention will be more clearly understood from the following detailed description taken in conjunction with the accompanying drawings, in which.

DETAILED DESCRIPTION OF THE INVENTION

Figure 1:
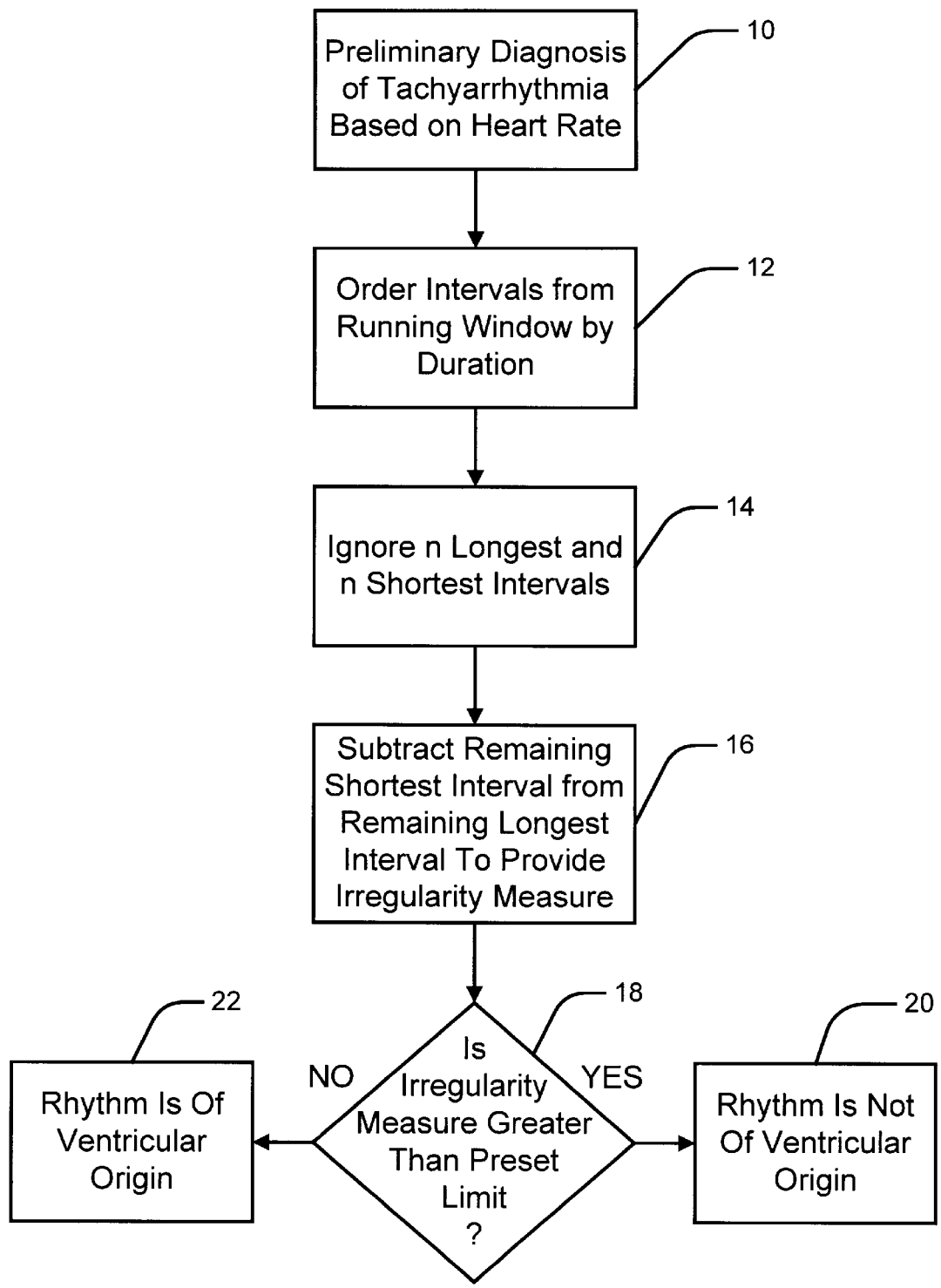
FIG. 1 is a flow chart illustrating the detection method of the present invention used to provide a measure of interval irregularity.

In overview, the present invention encompasses a novel detection algorithm which can be used in conjunction with a conventional diagnosis algorithm or can be used to provide a stand-alone measure of interval irregularity. The method of the invention enables discrimination between ventricular and supraventricular tachyarrhythmias. For example, the novel detection algorithm of the present invention can be used to independently qualify a cardiac episode which has been preliminarily diagnosed as a tachyarrhythmia as being either a ventricular or supraventricular tachyarrhythmia.

The inventor has discovered that not all intervals are needed to quantify heart rate variability (interval irregularity). By ignoring most of the intervals in an array or window and avoiding the need for any division, the computational demands of the method of the invention are substantially reduced.

Referring now to FIG. 1, the method of the invention will be described. A preliminary diagnosis of tachycardia is performed at step 10. This can be accomplished in any manner as is well known in the art. A simple method is to compute a running average for a sequence or window of R—R intervals and diagnose a tachycardia when the average falls below a preset tachycardia threshold. More complex methods such as the binning method disclosed in U.S. Pat. No. 4,971,058 mentioned above can also be used.

In step 12, the intervals from a running window are ordered based on duration. Thus, if there are N intervals, they are placed in order from shortest to longest with the shortest interval being identified as interval 1 and the longest interval being identified as interval N. A preselected number n of the shortest and longest intervals are then ignored at step 14. The parameter n is selected so that $0 \leq n < N/2$. The remaining shortest interval, i.e. interval n+1, is then subtracted from the remaining longest interval, i.e. interval N−n at step 16. The result is a measure of the variability or irregularity of the intervals in the window. Thus, if n=1, and N=8, interval 1 and interval 8 are ignored and interval 2 (n+1=2) is subtracted from interval 7 (N−1=7). If n=0, the shortest interval is subtracted from the longest interval. In a preferred embodiment, n is selected to be greater than zero to allow the diagnosis to be insensitive to n sense errors in the window, such as missed R waves or premature ventricular contractions (PVCs) mistaken for R waves. At step 18, the irregularity measure is compared to a preset limit. If the irregularity is greater than the preset limit, it is determined at step 20 that the rhythm is not of ventricular origin. Thus, the rhythm could be for example conducted atrial fibrillation which would not receive therapy or would receive a different therapy than a ventyricular arrhythmia. If the irregularity measure is less than or equal to the preset limit, it is determined that the rhythm is of ventricular origin, such as ventricular tachycardia.

In an alternative method of the invention, a running measure of interval irregularity may be provided. With this method, step 10 of FIG. 1 is omitted and the remaining steps are continuously performed for each new interval which the ICD measures. Thus, the oldest interval is discarded from the running window and the newest interval is added.

In another alternative embodiment of the invention, the need to specifically order the intervals in an array of intervals of length N is avoided. This method may be preferred since it may be computationally less intensive than the ordering method (at least for small n). Specifically, it allows the identification of the n+1 smallest and n+1 largest intervals in the array without completely ordering the array. For example, for n=1, the method will identify the second (next) smallest and second (next) largest intervals in the array and then the difference between these two values may be taken. In the method for n=1, variables representing the Largest Interval (LI) and Next Largest Interval (NLI) are initialized to zero. Then variables representing the Smallest Interval (SI) and Next Smallest Interval (NSI) are initialized to the largest value recognized by the hardware. The method then proceeds through the unsorted array of size N until all intervals have been processed. The Current Interval (CI) is compared to LI. If CI>LI, then replace NLI with LI and replace LI with CI. Otherwise, if CI>NLI, replace NLI with CI. If the Current Interval is not larger than either the Largest Interval or the Next Largest Interval, it is then compared with the Smallest Interval. If CI<SI, then replace NSI with SI and replace SI with CI. Otherwise, compare CI to NSI and if CI<NSI then replace NSI with CI. Proceed to the next interval until all of the intervals have been processed. When finished with all the intervals in the array, NLI contains the second largest interval, and NSI contains the second smallest interval.

In yet another alternative embodiment, the intervals also do not need to be ordered by interval length. An array of N intervals is selected and is scanned retaining the longest interval in a first memory location and replacing its value with zero. This is repeated n times, saving the last value that is obtained in the first memory location. All N intervals (with the largest interval(s) having been replaced with zeros) are then scanned retaining the shortest nonzero value in a second memory location. It's value is replaced with 999 (or some other large number). This is repeated n times, saving the last value that is obtained in the second memory location. The value in the second memory location is then subtracted from the value in the first memory location to provide the interval irregularity measure. It will be appreciated by those skilled in the art that the actual interval lengths are not discarded when they are replaced in this algorithm but are retained for other purposes.

It will be readily appreciated by those skilled in the pertinent art that the present invention also encompasses a cardiac therapy device, e.g., an ICD, programmed to implement the tachyarrhythmia detection method of the present invention. In this regard, it is a routine matter to those of ordinary skill in the pertinent art to write the code constituting the software (computer program) for programming the ICD (or other cardiac therapy device), using readily available programming tools. Further, although the detection algorithm has been described hereinabove in terms of sensing intervals between successive heartbeats, it should be clearly understood that the term "heartbeats" is intended in a generic sense to mean "cardiac events", e.g., QRS complexes.

Although the present invention has been described in detail hereinabove, it should be clearly understood that many variations and/or modifications of the basic inventive concepts herein taught which may appear to those skilled in the pertinent art will still fall within the spirit and scope of the present invention, as defined in the appended claims.

What is claimed is:

1. A method for analyzing a cardiac rhythm, including the steps of:

detecting a patient's cardiac activity, said cardiac activity including successive heartbeats, and providing a sequence of cardiac intervals which are measures for the time between sequential ones of said successive heartbeats;

selecting a window containing a predetermined number N of successive cardiac intervals;

ignoring a predetermined number n of the shortest and longest ones of said intervals where $0 \leq n < N/2$; and taking the difference between the remaining longest and shortest intervals where said difference provides a measure of interval irregularity whereby said measure of interval irregularity is indicative of whether the cardiac rhythm is of supraventricular or ventricular origin.

2. The method as set forth in claim 1, wherein said step of ignoring a selected number of the shortest and longest ones of said intervals includes ordering said intervals from shortest to longest with the shortest being interval 1 and the longest being interval N and taking the difference between interval N−n and interval n+1.

3. The method as set forth in claim 1, and further including the step following said detecting step and before said selecting a window step of determining from said sequence of cardiac intervals whether a prescribed tachycardia rate threshold has been exceeded.

4. A method for analyzing a cardiac rhythm, comprising the steps of:

detecting a patient's cardiac activity including a sequence of successive cardiac intervals;

determining from said detected cardiac activity a heart rate for said patient and determining if said patient's heart rate exceeds a preselected tachycardia rate threshold;

if said patient's heart rate exceeds said preselected tachycardia rate threshold, selecting a window of successive cardiac intervals;

ignoring a predetermined number of the shortest and longest ones of said intervals in said window; and taking the difference between the remaining longest and shortest intervals to provide a measure of interval irregularity.

5. A method for providing a measure of cardiac interval irregularity, including the steps of:

detecting a patient's cardiac activity including a sequence of heartbeats and providing a sequence of intervals that are measures for the time between successive heartbeats;

ignoring a preselected number of the shortest and longest ones of said intervals; and taking the difference between the remaining longest and shortest intervals to provide a measure of interval irregularity.

6. The method as set forth in claim 5, and wherein:

said detecting step includes the step of selecting a window of N successive cardiac intervals;

said ignoring step includes the step of setting a parameter n such that $0 \leq n < N/2$ and further includes the step of ordering said intervals from shortest to longest with the shortest being interval 1 and the longest being interval N; and said step of taking the difference includes taking the difference between interval n+1 and interval N−n to provide the measure of interval irregularity.

* * * * *